United States Patent [19]

Herrmann et al.

[11] Patent Number: 5,492,591
[45] Date of Patent: Feb. 20, 1996

[54] MODULAR APPARATUS FOR FABRICATING AN ABSORBENT ARTICLE

[75] Inventors: Thomas R. Herrmann, Redding, Calif.; Donald J. Teodoro, Kent, Wash.

[73] Assignee: Paragon Trade Brands, Inc., Federal Way, Wash.

[21] Appl. No.: 316,127

[22] Filed: Sep. 30, 1994

Related U.S. Application Data

[62] Division of Ser. No. 942,926, Sep. 10, 1992, Pat. No. 5,383,988.
[51] Int. Cl.⁶ ..................................................... B32B 35/00
[52] U.S. Cl. .......................... 156/538; 156/349; 156/539; 156/543; 156/552; 156/598; 604/358
[58] Field of Search ..................................... 156/349, 538, 156/539, 543, 552, 598; 604/358

[56] References Cited

U.S. PATENT DOCUMENTS

| | | |
|---|---|---|
| 3,741,842 | 6/1973 | Joa . |
| 3,758,363 | 9/1973 | Frick . |
| 4,081,301 | 3/1978 | Buell . |
| 4,106,972 | 8/1978 | Caudill . |
| 4,726,168 | 2/1988 | Seko . |
| 4,915,282 | 4/1990 | Martin . |
| 5,235,515 | 8/1993 | Ungpiyakul . |

FOREIGN PATENT DOCUMENTS

| | | |
|---|---|---|
| 0230137 | 12/1986 | European Pat. Off. . |
| 0267861 | 3/1987 | European Pat. Off. . |
| 0396512 | 4/1990 | European Pat. Off. . |

Primary Examiner—David A. Simmons
Assistant Examiner—M. Curtis Mayes
Attorney, Agent, or Firm—Dressler, Goldsmith, Shore & Milnamow, Ltd.

[57] ABSTRACT

A system for fabrication of absorbent articles includes a linear array of frame modules each having an open interior. Panels are mounted to one face of the modules. Article fabrication mechanisms are mounted to project from the panels. Operating means are disposed within the modules and are operatively engaged through the panels with the fabrication mechanisms. An operating and control system is provided for a machine in which disposable absorbent articles are fabricated. Continuously operating mechanisms are driven by electric motors for continuously operating on moving webs and other components of the article. A main drive shaft is rotated for transferring power through direction phasing mechanical power transfer devices to mechanisms which intermittently effect unity operations with respect to an associated moving web. The direction phasing mechanical power transfer devices are controlled relative to a sensed portion of an article component so as to temporarily vary the speed of the unity operation and effect registration of the operation in a preselected relationship with the associated moving web.

13 Claims, 9 Drawing Sheets

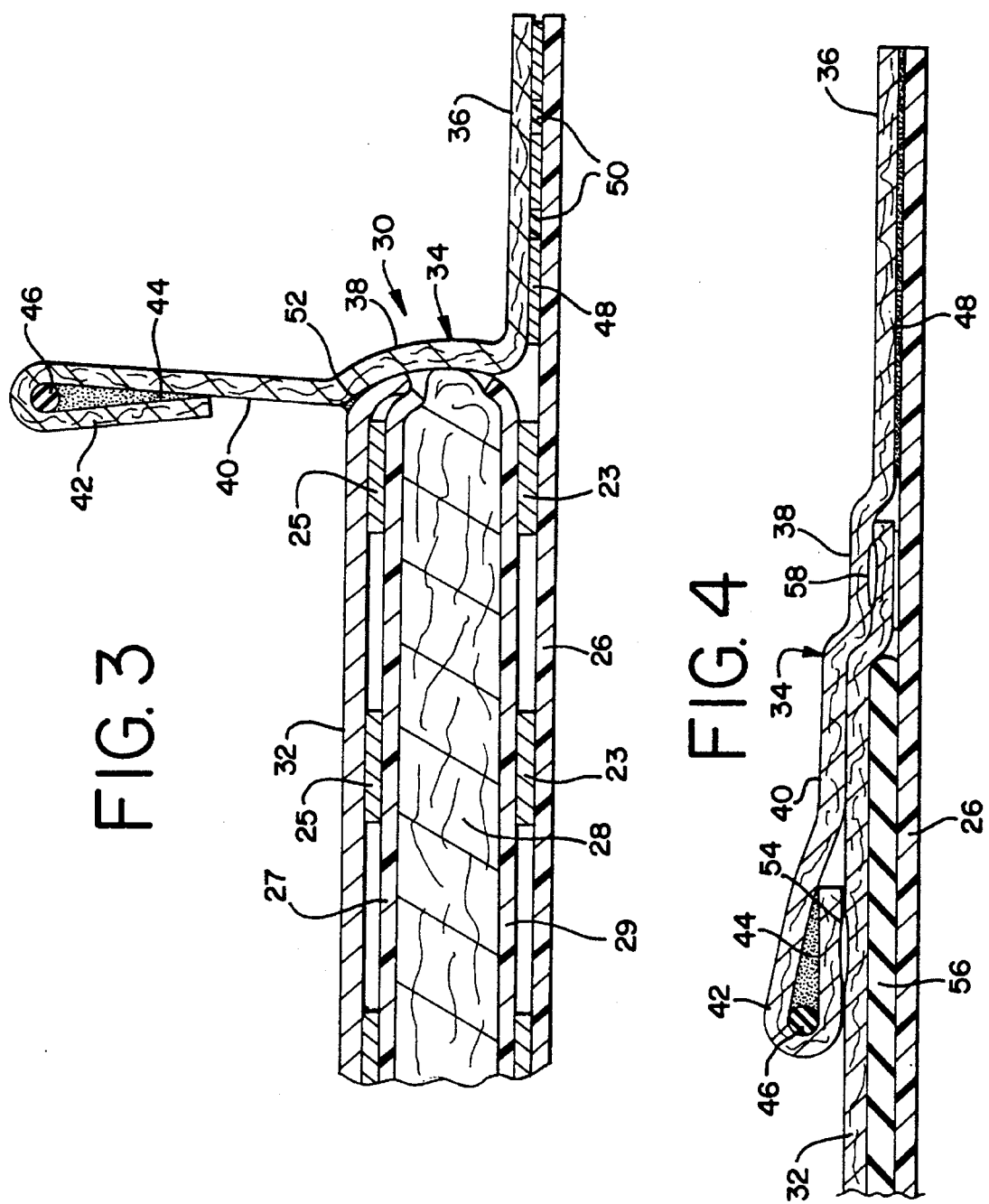

MODULAR APPARATUS FOR FABRICATING AN ABSORBENT ARTICLE

This application is a division, of application Ser. No. 07/942,926, filed Sep. 10, 1992, now U.S. Pat. No. 5,383,988, issued Jan. 24, 1995.

TECHNICAL FIELD

The present invention relates to the manufacture of disposable, absorbent articles such as diapers, sanitary pads, and the like. More particularly, the present invention relates to methods and apparatus for manufacturing a variety of such articles efficiently and at high speeds on apparatus that accommodates flexible manufacturing programs and that facilitates installation, modification and service.

BACKGROUND OF THE INVENTION AND TECHNICAL PROBLEMS POSED BY THE PRIOR ART

Disposable, absorbent articles typically include a thin, flexible, liquid-impermeable backsheet, an absorbent pad or panel on the backsheet, and an overlying, liquid-permeable topsheet. Each of these components can be typically supplied in the form of a continuous web by an apparatus which forms, guides, combines, and secures the components together.

In addition, some types of disposable, absorbent articles, such as diapers, typically include other components, such as elastic bands in the crotch area of the article to provide enhanced containment and leakage-resistance. Other features may include adhesive-coated tape tabs for securing the article to the wearer, a landing zone target tape against which the tape tabs can be securely, yet removably applied, and front and rear waist elastic elements to provide enhanced fit and comfort.

While a variety of different mechanisms have been developed for combining the above-discussed components to form a completed article, it is preferable to employ such mechanisms along a processing line for controlled operation together to fabricate the article on a continuous basis as the major components move along the processing line.

It is also desirable to operate an absorbent article manufacturing line at relatively high speeds so as to produce completed articles at a relatively high production rate. Depending upon the nature of the article, and upon the number of features in the article, manufacturers may attempt to achieve production rates on the order of hundreds of units per minute. When absorbent article component assembly mechanisms are operated at high speeds, the proper component processing operations, such as registration, cutting, bonding, etc., become more difficult.

These processing problems are exacerbated by the fact that absorbent articles are typically fabricated from continuous webs of material which are assembled on a continuously moving basis along the length of the articles while some discrete components of other material are intermittently applied to the webs. A continuously moving web could be a backsheet web or a topsheet web which is continuously conveyed through a processing line for being severed to form articles of selected lengths, and the conveying mechanisms and supply roll associated with the movement of these web components would generally operate continuously.

Other mechanisms in an absorbent article manufacturing system operate intermittently on a moving web or other component of the article. For example, a pair of tape tabs may be placed at predetermined intervals along a moving web so that each article that is ultimately formed has a pair of properly located tape tabs. Another example of such an intermittent operation is the transverse severing of an assembly of webs so as to separate the individual, completed articles.

Such intermittent processes may be described as "unity operations" which are typically effected relative to at least one associated moving web once per each article. Such a unity operation must be timed and controlled to occur at a precise location on, or relative to, the moving web. The unity operation must thus be controlled relative to the speed of the web.

Further, owing to tolerances in the operating mechanisms, slippage of the absorbent article components along the processing line, etc., precise registration of such unity operations with the moving web or webs is difficult, and becomes especially difficult at high line speeds. Accordingly, it would be advantageous to provide an improved system for effecting unity operations in a controlled manner relative to the continuous operations and relative to actual selected locations on moving webs.

Further, it would be desirable to provide such an improved system with means for efficiently transferring power to a plurality of unity operators in an absorbent article manufacturing line. Also, it would be advantageous to provide such a power transmission system with a design that could accommodate relatively easy installation, service, and adjustment of the mechanisms.

Changing market conditions may require a manufacturer to quickly modify its products or provide new products. Further, flexible manufacturing techniques and programs are nowadays becoming more frequently employed by manufacturers to accommodate, in one manufacturing system, the sequential production runs of a number of different products. To this end, it would be desirable to provide an improved system for an absorbent article manufacturing apparatus which would operate in a way that would more readily accommodate product changes or modifications.

In particular, it would be beneficial if such an improved system could function to mount and support absorbent article manufacturing mechanisms in a manner that would accommodate relatively rapid installation, servicing, and adjustment of such mechanisms.

It would also be desirable for such an improved system to accommodate expansion of the manufacturing line by the addition of mechanisms that would provide alternative or additional features on an absorbent article product.

Further, it would be advantageous if such an improved system could readily accommodate changes in the placement or location of selected mechanisms along the processing line, and such an improved system should preferably require only a minimum number of different support components so as to reduce manufacturing complexity and simplify installation.

The present invention provides an improved absorbent article manufacturing system which can accommodate designs having the above-discussed benefits and features.

SUMMARY OF THE INVENTION

A system for in-line fabrication of disposable absorbent articles in accordance with the principles of one aspect of the present invention includes a novel structure for supporting components or mechanisms of an apparatus or machine for manufacturing the articles.

In particular, a plurality of substantially identical frame modules are provided for being joined together. Each module has an open interior and open faces. The modules are joined in a linear array to define a front face therealong.

A plurality of substantially identical panels are each mounted to one of the modules along the front face of the array. The panels are each selectively mountable on selected ones of the modules. In a preferred embodiment, the modules each have a generally rectangular parallel parallelpiped configuration, and two panels are mounted on the front face of each module, one above the other.

The absorbent article fabrication mechanisms, such as conveyors, adhesive appliers, web severing mechanisms, are mounted to project from, or on, the panels outwardly of the modules to facilitate operator access to the mechanisms.

A plurality of operating means for operating a plurality of the mechanisms are provided inside the modules. Each operating means is mounted so as to be operably engaged through a panel with an associated fabrication mechanism.

In a preferred embodiment, the modules are joined together by elongate connecting members for spacing adjacent modules apart by a distance equal to the module width as measured along the length of the linear array of modules. Panels can be mounted to the elongate connecting members between the adjacent modules, and absorbent article fabrication mechanisms can be mounted on or through the panels to project from the fronts of the panels. The mechanisms can be operated by operating means mounted behind the panels within the framework defined by the modules. The operating means, such as motors, are operatively engaged with the fabrication mechanisms through the panels.

The novel modular structure is effective in mounting the fabrication mechanisms for easy access, observation, and adjustment. The modular nature of the structure accommodates expansion of the system or relocation of fabricating mechanisms to desired positions along the processing line. Access to the operating means, such as motors, gear drives, etc., is facilitated by the open framework of the modules behind the panels.

According to another aspect of the invention, a novel method and apparatus are provided for operating a machine in which disposable absorbent articles are fabricated along at least one processing path. The method and apparatus are especially suitable for articles fabricated from components which include webs of material assembled by (1) a plurality of first, continuous operating means for each continuously operating on at least one moving web (e.g., as with a web conveyor) and (2) a plurality of second operating means for each effecting a unity operation intermittently relative to at least one associated moving web at least once per each absorbent article (e.g., as with a web severing knife).

The method and apparatus function together as a drive system and control system for operating a plurality of individual drive means (such as adjustable speed electric motors) for each respectively providing power to respective ones of the continuous operating means. A selected one of the drive means is adjusted to establish a preselected speed of a selected one of the continuous operating means.

The remaining drive means are controlled to adjust the speeds of the remaining continuous operating means so as to be equal the preselected speed of the selected continuous operating means.

A main drive shaft is rotated at a speed proportional to the preselected speed of the selected one continuous operating means for transferring power from the shaft to the plurality of second operating means through a plurality of direction phasing mechanical power transfer devices each associated with at least one of the second operating means. Each of the direction phasing mechanical power transfer devices can be adjusted to temporarily change the speed of the associated second operating means relative to the speed of the drive shaft to effect registration of the operation of the second operating means in a preselected relationship with the associated web portion.

In a preferred form of operation, identical component features (e.g., the severed, leading edge of an absorbent panel) are provided so as to be generally equally spaced along the processing path for each being subsequently associated with a different one of the articles as the articles are assembled seriatim. The desired spacing of these features is initially established as a reference spacing. Thereafter, during routine operation, the successive spacings are compared with the reference spacing. If there is a difference, at least one of the associated direction phasing mechanical power transfer devices is then temporarily adjusted relative to the speed of the drive shaft as a function of the difference between the reference spacing and a subsequently measured successive spacing. This adjustment temporarily increases or decreases the speed of the associated second operating means and effects registration of the operation of the second operating means in a preselected relationship with the associated web portion.

In a preferred embodiment, feedback controls are incorporated. The speed of the selected one continuous operating means is measured. An electronic feedback means is employed for comparing the measured speed with the preselected speed and for controlling the selected one drive means (e.g., motor) to maintain the selected one continuous operating means at the preselected operating speed.

Also, in a preferred form of the system, the speed of at least one of the remaining continuous operating means is measured. An electronic feedback means is employed for comparing the two measured speeds and for controlling one of the drive means to maintain the operating speed of the one remaining continuous operating means at a speed equal to the speed of the selected one continuous operating means.

The above-described novel operating system permits a single, main drive shaft to be employed for efficiently actuating all, or a selected number, of the unity operations (e.g., a target tape applier, web severing knife, etc.).

Further, the use of a direction phasing mechanical power transfer device associated with the actuation of a unity operation accommodates (1) the sensing of the actual positions or spacings of the absorbent article features and (2) the control of the unity operation so as to either retard or advance the actuation of the unity operation and thereby effect such actuation at the proper location on the article.

The system further accommodates the use of a main drive shaft driven by a continuously operating, adjustable speed electric motor so as to establish a drive shaft rotation speed that corresponds to the speed of the selected one continuous operating means.

In a preferred embodiment, a primary continuous operating means, such as a laminator drum, is driven by a single, DC motor. The other continuous operating means motors are controlled to operate at the same speed as the laminator drum drive motor, and the primary drive shaft is rotated by a separate DC motor which is also controlled at a speed corresponding to, or proportional to, the speed of the laminator drum motor. The phasing of the individual unity operations from the main drive shaft can be readily controlled through the use of conventional phasing devices.

The above-described drive system and control system employed with the continuous operating means and with the operating means for the intermittent unity operations can be readily installed in the above-described modular support system. This provides easy accessibility to operating drives and components such as phasing devices, other controls, belts, gearboxes, bearings, etc. while at the same time accommodating the addition or relocation of mechanisms as well as the expansion of the system.

Numerous other advantages and features of the present invention will become readily apparent from the following detailed description of the invention, from the claims, and from the accompanying drawings.

BRIEF DESCRIPTION OF THE DRAWINGS

In the accompanying drawings that form part of the specification, and in which like numerals are employed to designate like parts throughout the same.

FIG. 3 is a fragmentary, cross-sectional view taken along lines 3—3 of FIG. 2;

FIG. 4 is a fragmentary, cross-sectional view taken generally along lines 4—4 of FIG. 2;

DESCRIPTION OF THE PREFERRED EMBODIMENTS

While this invention is susceptible of embodiment in many different forms, this specification and the accompanying drawings disclose only some specific forms as examples of the invention. The invention is not intended to be limited to the embodiments so described, however. The scope of the invention is pointed out in the appended claims.

For ease of description, the apparatus of this invention is described in the normal (upright) operating position, and terms such as upper, lower, horizontal, etc., are used with reference to this position. It will be understood, however, that the apparatus of this invention may be manufactured, stored, transported, used, and sold in an orientation other than the position described.

Some of the figures illustrating an embodiment of the apparatus show structural details and mechanical elements that will be recognized by one skilled in the art. However, the detailed descriptions of some of such elements are not necessary to an understanding of the invention, and accordingly, are not herein presented.

With reference now to the drawings, therein is illustrated a disposable absorbent garment 10 or disposable diaper which is but one of many forms of an absorbent article that can be fabricated in accordance with the principles of the method and apparatus of the present invention. As used in the present disclosure, the term "diaper" is intended to refer to an absorbent garment which is worn by an individual for absorbing body fluids, such as urine and/or fecal matter.

It is to be understood that garments manufactured by methods and apparatus embodying the principles of the present invention can be appropriately sized for use by infants and children, and can further be sized for use by incontinent adults. Additionally, absorbent articles embodying the present invention may take the form of absorbent pads, sanitary products, absorbent diaper inserts, and the like.

Figure 2:
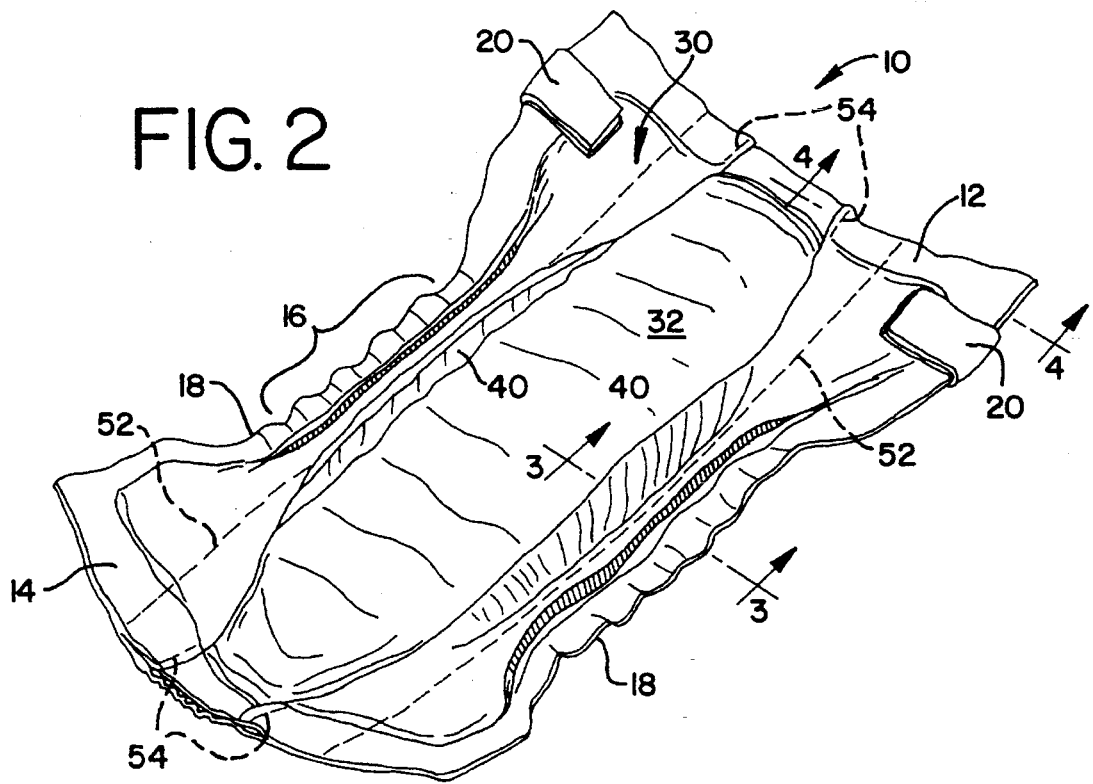
FIG. 2 is a top perspective view of the absorbent garment generally in a form prior to use.

The garment 10 is described in detail in the commonly assigned, copending U.S.A. patent application Ser. No. 07/608,809 filed Nov. 5, 1990, the disclosure of which is incorporated by reference thereto to the extent not inconsistent herewith. With particular reference to FIG. 2, the absorbent garment 10 includes a rear waist portion 12, a front waist portion 14, and a crotch area 16 extending between the front and rear waist portions. The crotch area of the garment generally corresponds to that portion which is positioned between the legs of a wearer during use. As the term "crotch area" is used herein, it refers to that part of the garment which comprises between about onethird and three-fourths of the longitudinally central portion of the garment 10.

For enhanced fit and comfort, the garment 10 has a generally I-shaped, contoured configuration, with the crotch area 16 being relatively narrow by virtue of the formation of leg cutouts 18 at each of the side margins of the garment.

Figure 1:
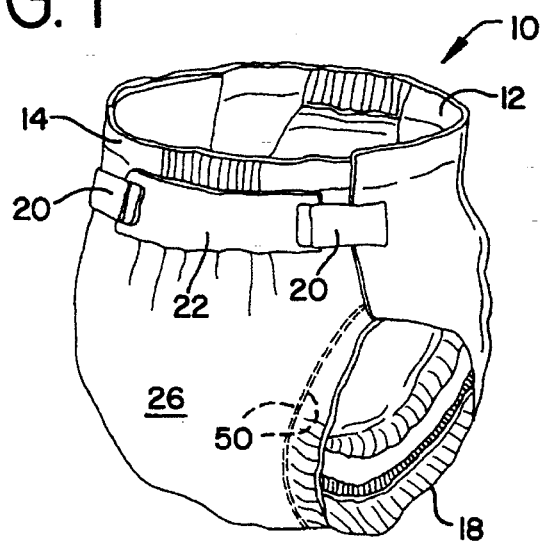
FIG. 1 is a perspective view of a disposable, absorbent garment in the form of an infant diaper which is illustrated generally as it appears when being worn and which can be fabricated in accordance with the teachings of the present invention.

Convenient securement of the absorbent garment 10 to a wearer is facilitated by the provision of a pair of adhesive-coated tape tabs 20 at respective opposite sides of the rear waist portion 12 of the garment. The tape tabs 20 are positioned for securement to the outside surface of the front waist portion 14, as illustrated in FIG. 1, and to this end, a tape landing zone or target tape 22 is preferably provided. The landing zone or target tape 22 typically comprises a strip of polymeric sheet material to which the tape tabs 20 can be securely, yet removably applied, with the landing zone target tape 22 desirably acting to reinforce the front outside surface of the garment 10 so that removal and reapplication of the tape tabs 20 does not damage the garment 10.

With reference to FIGS. 1, 3, and 4, the absorbent garment 10 includes a preferably liquid-impermeable backsheet 26 which generally defines the outer surface of the garment. The liquid impermeable characteristics of the backsheet act to prevent leakage of liquid through the backsheet for the desired containment characteristics. A wide variety of suitable polymeric film materials can be employed for the backsheet 26, such as a polyethylene sheet having a thickness on the order of between about 0.0005 and about 0.001 inches. Polyethylene terephthalate sheet material having a thickness of approximately 0.0005 to 0.001 inches may alternately be employed. Nonwoven materials exhibiting liquid-impermeability can be used, as can composite or laminate sheet materials such as comprising integrated nonwoven fabric and polymeric film layers.

The absorbent garment 10 further includes an absorbent panel 28 (FIG. 3) positioned on top of the backsheet 26. The absorbent panel preferably comprises an absorbent matrix including comminuted wood pulp, sometimes referred to as wood fluff, and superabsorbent material, which may comprise superabsorbent polymers or the like. Absorbent matrices comprising blends and/or layers of such absorbent materials can be employed. If desired, the superabsorbent material may be more heavily concentrated in specifically selected regions of the absorbent panel 28. Additionally, an absorbent matrix formed in accordance with U.S. Pat. No. 4,573,988, to Pieniak, comprising a compressed composite absorbent structure including a resilient web of fibers having superabsorbent material incorporated therein, can be used.

In a preferred embodiment, the absorbent panel 28 includes an exterior, liquid-permeable covering preferably comprising a top tissue layer 27 and a bottom tissue layer 29. These layers are held in position around the panel 28 by the other garment components.

Specifically, the bottom tissue layer 29 is adhesively secured with lines of adhesive 23 (FIG. 3) to the backsheet 26. The top tissue layer 27 is adhesively secured with lines of adhesive 25 to a topsheet assembly 30 (FIGS. 2 and 3).

The topsheet assembly 30 includes three components and is positioned on top of the top tissue layer 27 of the absorbent panel 28. The three-component topsheet assembly 30 includes a central liquid-permeable portion or sheet 32 which generally overlies, and is adhesively secured to, the absorbent panel 28, and a pair of side marginal portions or sheets 34 joined to respective opposite side edges of the central portion 32.

As best shown in FIG. 3, each of the side marginal portions 34 of the topsheet assembly 30 includes a plurality of segments which, at least in the crotch area 16 of the diaper, are arranged relative to central portion 32 and absorbent panel 28 to provide enhanced containment and leakage-resistance.

Specifically, each side marginal portion 34 includes a first outer segment 36 juxtaposed and joined to the underlying backsheet 26 laterally outwardly of the side edge of absorbent panel 28. Each side marginal portion 34 further includes a second, intermediate segment 38 adjacent the first segment 36 and positioned generally inwardly thereof. A third, standing gather segment 40 of each side marginal portion 34 is positioned adjacent the second, intermediate segment 38, and is configured to provide one of the two inner standing gather constructions of the garment.

To this end, each standing gather segment 40 includes an overturned free edge to thereby define a sleeve portion 42. In accordance with the illustrated embodiment, it is presently preferred that the free edge of each standing gather be overturned inwardly toward the longitudinal centerline of the absorbent garment 10, particularly when the longitudinal end portions of each standing gather are secured inwardly, as will be further described.

The sleeve portion 42 of each standing gather segment 40 is secured in its overturned position by suitable bonding of the segment to itself, with a spray adhesive 44 being presently preferred. In order to achieve the desired gathering effect for each standing gather segment, at least one elastic element 46 extends within the sleeve portion 42 along at least the crotch area 16 of the garment. While various techniques may be employed, it is presently preferred that the standing gather elastic element 46 be applied to the nonwoven material from which the side marginal portion 30 is formed by securing the elastic to the nonwoven material with the elastic in an extended or stretched condition. The adhesive 44 is preferably employed for both securing the elastic element 46 to the standing gather segment 40, as well as for formation of sleeve portion 42.

In the illustrated embodiment, including the hourglass-shaped absorbent panel 28, each of the second intermediate segments 38 and the third standing gather segment 40 are of a substantially constant dimension throughout the length of the garment 10. In contrast, each first outer segment 36 varies in dimension, being relatively narrow at the crotch area 16 of the garment, and relatively wider at each of the front and rear waist portions 12 and 14 whereat the absorbent panel 28 extends beneath each intermediate segment.

With further reference to FIG. 3, any of a variety of techniques may be employed for securing the first segment 36 of each side marginal portion 34 to the associated backsheet 26. It is presently preferred that a spray adhesive 48 be used for this purpose. It is also presently preferred that one or more leg elastic elements 50 be provided in this region to thereby elasticize each leg opening, generally at each leg cut-out 18, for the desired fit and containment. In the illustrated embodiment, a pair of leg elastic elements 50 are provided between first segment 36 and backsheet 26, with the spray adhesive 48 acting to secure the elastic elements in position. In accordance with known formation techniques, elastic elements 50 are integrated with the associated backsheet 26 and topsheet assembly 30 in an extended or stretched condition, whereby the absorbent garment 10 is effectively gathered to form an elastically extensible structure.

As illustrated, opposite side edges of central portion 32 of topsheet assembly 30 are respectively joined to the side marginal portions 34. Specifically, each of the side edges of the central portion 32 is joined to the respective one of the side marginal portions 34 generally at the juncture of the second and third segments 38 and 40 of the side marginal portion 34. While standard gluing methods can be used, it is presently preferred that this be achieved by the provision of a sonic bond 52 which extends longitudinally of the garment (generally as illustrated in phantom line in FIG. 2) thereby integrating the topsheet assembly 30.

Significantly, this relative disposition of the sonic bond 52 acts to space the side edge of the central portion 32, at least in the crotch area 16, from the backsheet 26 of the garment by approximately the dimension of the respective second intermediate segment 38. This preferred configuration has been found to desirably avoid formation of trough-like regions just inwardly of the standing gather segments 40, thereby acting to avoid collection of liquid in such regions, which collection is believed to contribute to leakage of the garment.

In the illustrated embodiment, the absorbent panel 28 is positioned substantially between second and third segments 38 and 40 of the side marginal portions 34, at least in the crotch area 16. While such an arrangement is desirable, normal manufacturing tolerances and variances can make it difficult to precisely align the bond 52 with the edge of the panel 28. Additionally, the nonwoven fabric from which central portion 32 is typically formed exhibits some extensibility, which can permit the base of each standing gather segment 40 to shift laterally outwardly.

Since it is most preferred that to avoid trough-like regions adjacent the standing gathers, the bonds 52 can be positioned generally at or just inwardly of the side edges of the panel 28. Even though portions of the panel may thus extend beneath the third standing gather segments 40, formation of the side marginal portions 30 from material exhibiting significant hydrophobicity has been found to abate leakage of liquid from those panel portions which extend beneath the standing gather elements. As will be appreciated, use of a relatively thin absorbent panel 28, and the desire to avoid forming trough-like regions adjacent the standing gathers, calls for the preferred disposition of bonds 52 generally on top of such a thin panel.

As shown in FIG. 2, the hourglass shape of absorbent panel 28, including the provision of laterally extending ear portions in the front and rear waist portions 12 and 14, results in the ear portions of the absorbent panel extending beneath the second intermediate segment 38 of each side marginal portion 34 in the waist portions of the garment. However, the nonwoven material from which the marginal portions are formed is preferably selected to exhibit sufficient hydrophobicity so as to substantially preclude the possibility of liquid from the ear portions of the absorbent panel moving toward the wearer of the garment. Additionally, materials which exhibit the desired hydrophobicity have further been found to provide enhanced strength, and stretch and tear resistance, thus promoting secure and convenient use of the tape tabs 20.

Referring to FIG. 4, the preferred configuration of each of the front and rear waist portions of the garment 10 is illustrated. As will be observed, it is preferred that the longitudinal end portions of each of the standing gather segments 40 of the side marginal portions 34 be secured inwardly to the central portion 32 of the topsheet assembly. To this end, a sonic bond 54 (FIG. 2) is preferably provided at each of the longitudinal end portions of the standing gather segments 40. As is also illustrated in FIG. 4, it is presently preferred that the garment 10 be provided with front and rear waist elastic elements 56, which may comprise suitable foam elastic material for enhanced fit and comfort. These elements 56 are secured with lines of conventional spray adhesive (not illustrated in FIG. 4) on the top to the topsheet side center portion 32 and on the bottom to the backsheet 26.

As noted above, it is preferred that the free edge of each standing gather segment 40 be overturned inwardly toward the garment centerline, particularly when the end portions of the standing gather segments 40 are secured inwardly as shown in solid line in FIG. 4. This is aesthetically preferred since the edge of the gathered material at sleeve portion 42 is generally concealed, and also acts to avoid the material edge contacting the wearer of the garment.

However, the standing gather segments can be otherwise configured. For example, although not illustrated, at least one of the longitudinal end portions of each standing gather segment 40 can be secured outwardly to at least one of the respective first and second segments 36, 38 in which event it can be desirable to have the free edge of each standing gather segment 40 be overturned outwardly away from the garment centerline. It might be desirable in some cases to secure the rearward longitudinal portions of the standing gather segments inwardly (to central portion 32) and the forward longitudinal portions outwardly (to at least one of the first and second segments 36, 38), thereby forming a pouch-like construction in the forward portion of the garment (which portion ordinarily receives the most liquid during use).

As will be appreciated, a wide variety of materials may be employed for fabrication of the composite topsheet assembly 30. Nonwoven fabric materials are presently preferred, with the side marginal portions 34 preferably comprising nonwoven materials exhibiting a relatively high degree of hydrophobicity. One suitable material for the side marginal portions is spunbonded polypropylene nonwoven fabric having a basis weight in the range of about 0.3 to 0.8 ounces/square yard and a bond area in the range of about 7% to 20%, with a basis weight of about 0.5–0.6 ounces/square yard and an 18% bond area being particularly preferred. When untreated, this material exhibits the desired degree of hydrophobicity. One commercially available material of this type is available from Fiber Web of America, Greenville, S.C., under the product designation Unicorn Celestra™.

The central portion 32 of the composite topsheet assembly may also comprise a polypropylene nonwoven fabric having a basis weight and bond area as described above for side marginal portions 34. While the central portion 32 of an absorbent garment embodying the present invention can be selected to exhibit relatively high or relatively low liquid impermeability, it is presently preferred that the central portion 32 be selected to exhibit significantly greater hydrophilicity, and thus greater liquid permeability, than side portions 34. To this end, polypropylene nonwoven material such as described above is ordinarily treated with a surfactant to achieve the desired hydrophilicity Alternately, a hydrophobic fabric having apertures to permit liquid passage therethrough may be employed.

The present construction has been found to provide desirably enhanced containment characteristics. By the arrangement of the bonds at 48 and 52, plus the use of the preferred hydrophobic material for side marginal portions 34, the marginal portions function in the nature of shields at the sides of the absorbent panel 28 to abate leakage. Additionally, the bonding of the marginal portions to the backsheet avoids the creation of gaps or the like through which leakage might otherwise leak from the construction.

According to the present invention, disposable absorbent articles may be fabricated by mechanisms which are operated and controlled in a unique manner. The above-described diaper garment 10 is an example of one such absorbent article that may be manufactured. A machine for in-line fabrication of such a garment 10 is diagrammatically illustrated in FIGS. 6A and 6B.

Specific mechanisms are provided along, and as part of, the machine for engaging, conveying, acting against, or otherwise operating on, or relative to, at least one associated web of the article being formed as the web moves along the machine. A unique, modular support structure for the machine components is illustrated in more detail in FIGS. 6–8 and is described hereinafter with respect to those figures. First, however, the basic operation of the machine will be described.

The mechanisms in the machine for operating on, or relative to, a moving web may include special or conventional mechanisms. The details of such mechanisms, and the detailed method of operation of such mechanisms, will be apparent to those having skill in the art and an understanding of the necessary functions of such mechanisms. The detailed descriptions of such mechanisms are not necessary to an understanding of the invention, form no part of the present invention, and accordingly are not herein presented. However, some brief descriptions of the location and purpose of some of the significant mechanisms are next presented to serve as examples of the types of mechanisms with which the operating system and support system of the present invention may be employed as described in detail hereinafter.

Figure 6A:
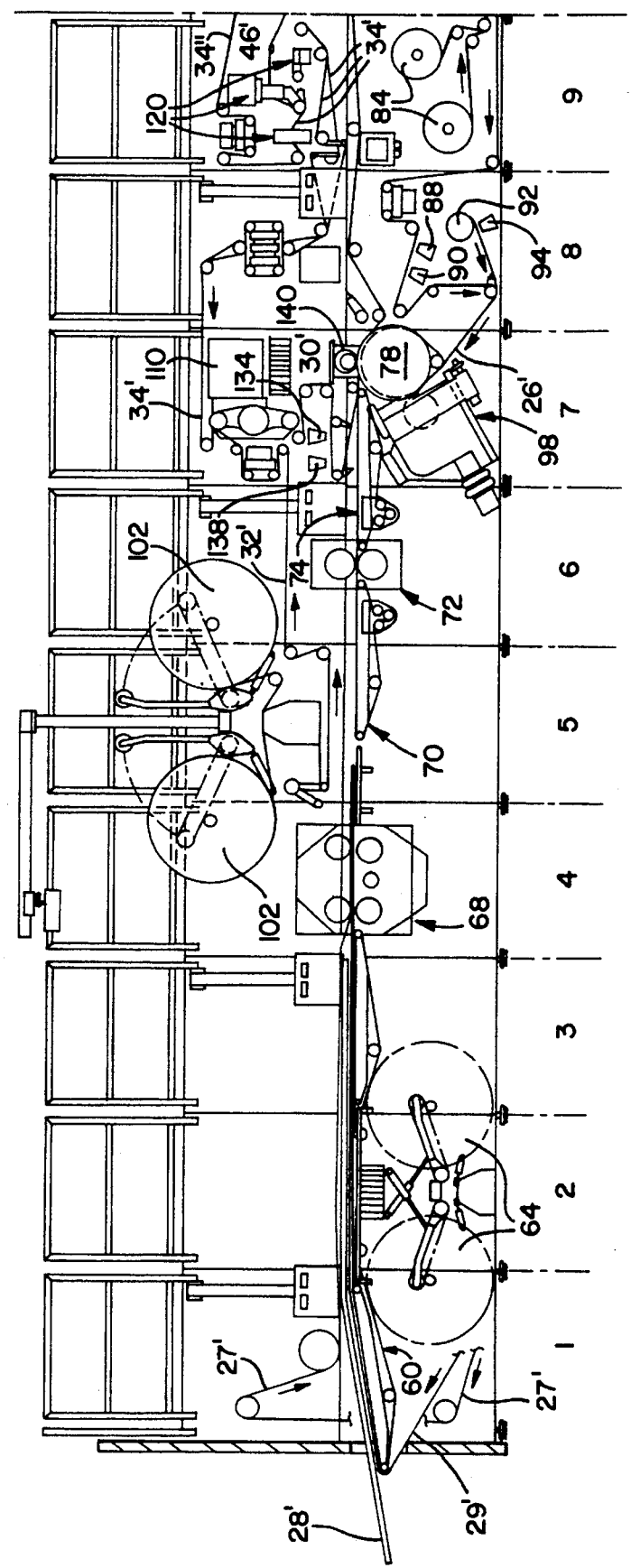
FIGS. 6A and 6B are simplified, partially schematic, diagrammatic side elevation views of a machine in which disposable absorbent articles are fabricated in-line in accordance with the present invention, FIG. 6A showing the left-hand half of the machine and FIG. 6B showing the right-hand half of the machine.
Figure 6B:
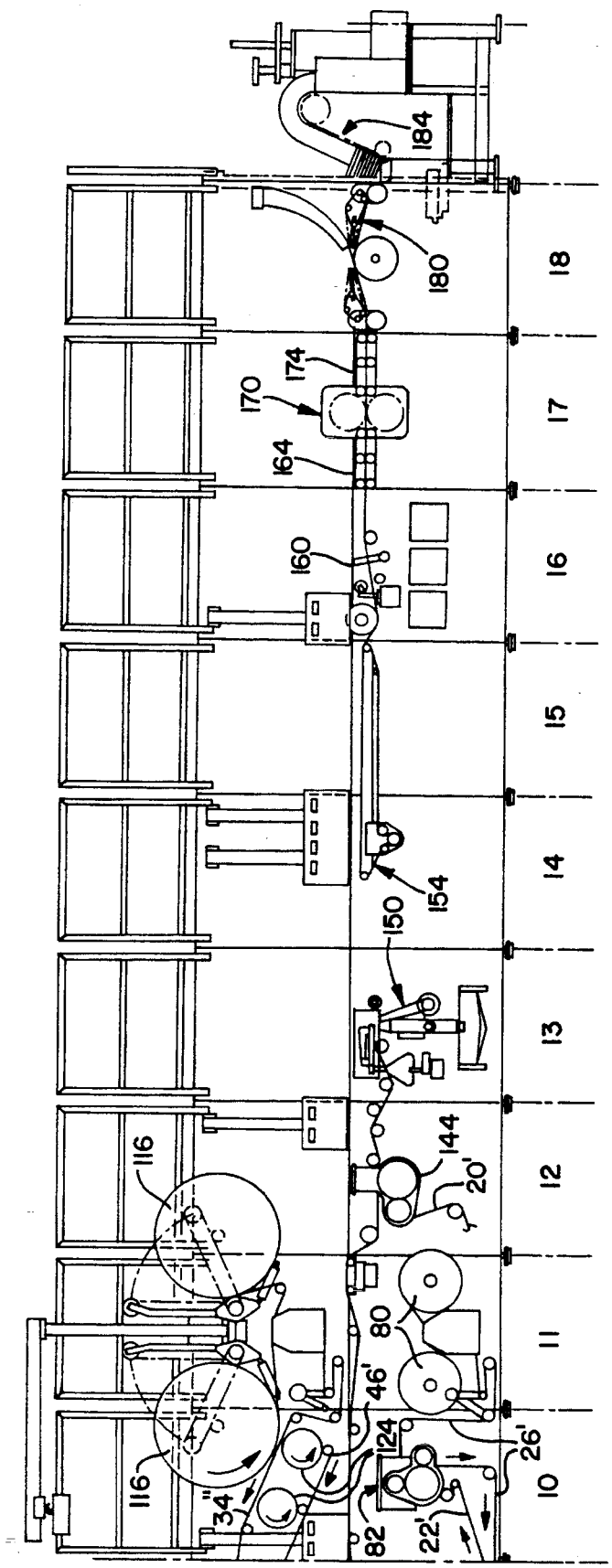

For convenient reference with respect to correlating FIGS. 6A and 6B with the accompanying description, the machine may be characterized as comprising 18 modules aligned in a linear array, and the modules are sequentially numbered 1–18 along the bottoms of FIGS. 6A and 6B. The locations of various mechanisms in the machine are specified in this description with reference to the associated module as identified by the corresponding number.

Referring first to the left-hand end of FIG. 6A, an absorbent panel web 28' is conveyed through the machine, and the absorbent panel web 28' is a continuous web of the material which constitutes the panel 28 as described above with respect to the garment 10 illustrated in FIGS. 1–5. The absorbent panel web 28' is supplied from a suitable bulk roll supply (not illustrated) which may be associated with a separate, conventional, in-feed mechanism but which may be operated from a motor and control system on the machine.

In other modes of operations, a conventional pocket former or drum former (not illustrated) may be provided upstream of the machine to form individual, contoured absorbent pads of blown, nonwoven fluff material. Such pads can be conveyed seriatim in a spaced array through the machine. Such a drum former could be operated and controlled directly by the machine.

The individual absorbent pads or the continuous, absorbent panel web 28' are conveyed down the machine processing line (toward the right as viewed in FIG. 6A) with a suitable, conventional conveyor 60. A conventional vacuum hold-down system (not illustrated) may be provided along the conveyor 60, and along other conveyors in the machine, to keep the web flat and to center the web so as to help insure proper registration of the various manufacturing operations. The mechanical and structural details per se of the conveyor 60, of the vacuum system, and of other similar conveyors and vacuum systems in the machine form no part of the present invention.

Figure 5:
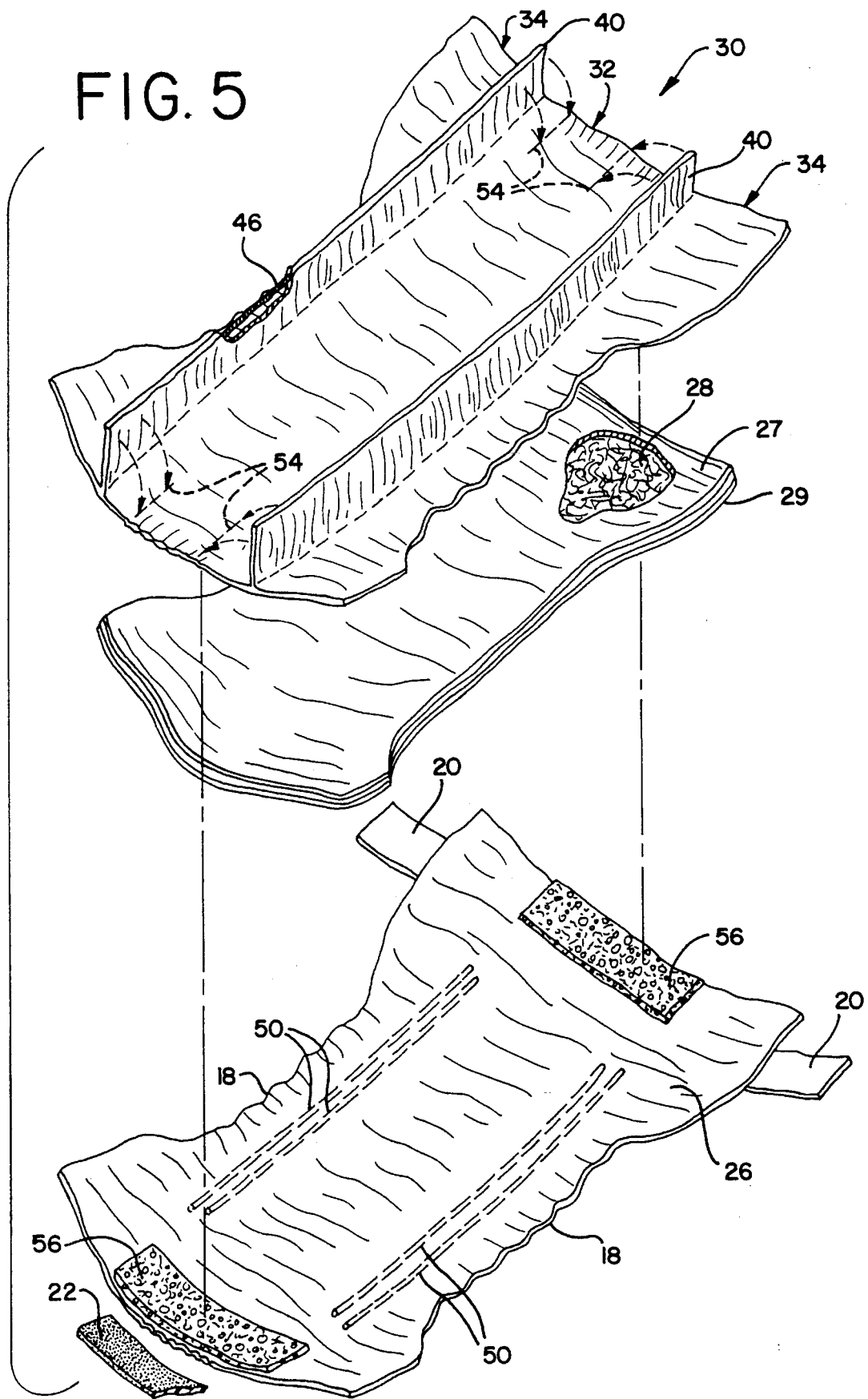
FIG. 5 is an exploded, perspective view of the absorbent article illustrated in FIGS. 1–4.

With reference to FIGS. 3 and 5, it will be recalled that the absorbent pad 28 is covered on the top with a top tissue layer 27 and on the bottom with a bottom tissue layer 29. As illustrated in module 1 (FIG. 6A), the top tissue layer is initially applied by the machine as a continuous top tissue layer web 27'. The bottom tissue layer is directed under the absorbent panel web 28' as a continuous bottom tissue layer web 29'. The tissue layer webs 27' and 29' are initially slit lengthwise (at a slitter (not illustrated)) from a common web supplied by one of two tissue supply rolls 64 located at the bottoms of modules 1, 2, and 3. The slitter, supply rolls 64, motor-driven unwind mechanisms, and other associated mechanisms operate in a conventional manner.

The sandwich assembly of the top tissue layer web 27', intermediate absorbent panel web 28', and bottom tissue layer 29' is conveyed through a conventional debulker 68 (module 4) which compresses the absorbent panel web 28' between the tissue layer webs 27', 29'.

The compressed sandwich assembly is moved forward from the debulker 68 by a conventional pad draw conveyor 70 (module 5) to a conventional pad knife mechanism 72 (module 6) which severs the three sandwiched web components at intervals to provide separate panel assemblies. The separate panel assemblies are conveyed downstream of the knife mechanism 72 by a conventional pad spacing conveyor 74 (module 6) which has a linear speed greater than the linear speed of the pad draw conveyor 70 so as to separate the individual pad assemblies and provide a desired end-to-end spacing.

The pad spacing conveyor 74 extends from module 6 to module 7 and feeds the spaced-apart panel assemblies to a conventional laminator drum 78 at which all of the other garment components and subassemblies are combined with the absorbent panel assembly. The other garment components and subassemblies are fabricated, partially assembled, and laterally registered in other mechanisms in the machine as will next be explained.

In particular, the backsheet 26 (FIG. 5) is initially supplied in the form of a continuous backsheet web 26' from one of two backsheet web supply rolls 80 (module 11 in FIG. 6B). The rolls 80 and associated operating mechanisms operate in a conventional manner.

As the backsheet web 26' leaves one of the supply rolls 80, it passes through a conventional target tape applier 82 (module 10) which applies the landing zone target tape 22 (FIGS. 1 and 5) to one surface of the backing sheet web 26'. The target tape 22 is supplied in the form of a continuous target tape web 22' from one of two target tape web supply rolls 84 (module 9 in FIG. 6A) which, together with associated conventional mechanisms, operate in a well-known manner.

The target tape applier 82 severs individual pieces of target tape 22 (FIGS. 1 and 5) from the target tape web 22' and bonds the pieces of target tape 22 by suitable conventional means to the appropriate locations along the backsheet web 26'.

The backsheet web 26' is drawn beyond the target tape applier 82 (module 10) past a conventional adhesive applier 88 (module 8) for applying lines of adhesive to the backsheet web 26' for attaching the foam waist gather elastic elements 56 (FIGS. 4 and 5) which are subsequently fed to the backsheet web 26' as is explained in detail hereinafter.

After leaving the adhesive applier 88, the backsheet web 26' passes a conventional adhesive applier 90 (module 8), and the adhesive applier 90 applies lines of adhesive 23 (FIG. 3) to the backsheet web 26' for attaching, at the laminator drum 78, the backsheet web 26' to (1) the absorbent panel bottom tissue layer web 29' and (2) the portions of the top sheet assembly 30 which extend beyond the absorbent panel assembly.

Between the laminator drum 78 and the adhesive applier 90, the continuous filament of leg elastic members 50 (FIGS. 3 and 5) are secured to the backsheet web 26' by means of a conventional device 92 that (1) provides a continuous length of elastic along the web 26', (2) splits the elastic into a plurality of continuous, parallel filaments containing the members 50, and tensions the elastic member filaments as the elastic member filaments are fed against the backsheet web 26'. A conventional adhesive applier 94 (module 8) applies adhesive 48 (FIG. 3) to the margins of the backsheet web 26' and/or to the portions of the filaments that will define the leg elastic members 50 when the assembled webs are subsequently severed transversely to separate the individual articles.

In module 7, the backsheet web 26' (now carrying the leg elastic members 50, the target tape 22, and the adhesive lines for securement of the foam waist gathering elastic members 56 and of the bottom tissue layer web 29') passes adjacent a conventional foam waist gather elastic member applier 98 (module 7). The applier 98 supplies pieces of foam waist gather elastic (56 in FIG. 5) and attaches them, at the laminator drum 78, to the backsheet web 26' on the adhesive lined receiving areas (not illustrated in FIG. 4). Actually, each foam piece applied to the web 26' is twice as long as an individual member 56 on a completed, separated garment 10. Each double length foam elastic piece is applied to the web 26' so that the piece lies centered over the ends of the two adjacent garments where the webs are subsequently transversely severed to form the separate garments then having correctly sized elastic members 56.

The apparatus 98 for applying the foam waist gather elastic element pieces applies each foam elastic element piece in a transversely stretched (i.e., tensioned) condition to the inner surface of the backsheet web 26'.

The backsheet web 26', with the double length foam waist gather elastic elements 56 now also in place at the laminator drum 78, is carried into engagement with the bottom of the pad assemblies being moved onto the laminator drum 78 by the pad spacing conveyor 72. The laminator drum 78 also functions to combine the backsheet web 26' and pad assemblies with a web 30' of topsheet assemblies 30 that has been fabricated by other machine components as will next be described.

Specifically, as previously noted, each article has a topsheet assembly 30 (FIG. 5) that includes a nonwoven topsheet center portion 32 and two topsheet side margins 34. The center portion 32 is supplied in the form of a topsheet center portion web 32' from one of two, conventional supply rolls 102 located in modules 4, 5, and 6.

The topsheet center portion web 32' is combined with two webs 34' of the topsheet side margins at a conventional ultrasonic bonding apparatus 110 to form a completed topsheet assembly web 30' which is then fed to the top of the laminator drum 78. Specifically, the two side margin webs 34' are fed in a parallel, spaced-apart orientation for being secured to the opposite side edges of the topsheet center portion web 32' (as with the ultrasonic bond 52 (FIG. 3)), and the side margin webs 34' ultimately become the discreet side margin portions 34 of the individual garments 10.

While being joined to the topsheet center portion web 34', the side margin webs 34' are drawn through the ultrasonic bonding apparatus 110 in a preformed condition wherein the standing gather sleeve portion 42 (FIG. 3) has been folded over and secured around the standing gather elastic element 46 with the adhesive 44 (FIG. 3).

The mechanisms for preforming the side margin webs 34' are located in modules 8, 9, 10, 11, and 12. In modules 10, 11, and 12 there are two side margin supply rolls 116 of conventional construction. A single, double width web 34" of side margin material is drawn off one of the supply rolls 116 to a multiple function, side margin-forming mechanism 120 (module 9).

The forming mechanism 120 slits the wide web 34" into the two equal width side margin webs 34'. The mechanism 120 also applies continuous, elastic filaments 46' to each side margin web 34' and folds the sleeve portion 42 over to secure it around the elastic filament 46'. The two elastic filaments 46' are provided in a parallel paths, each filament 46' being supplied from one of two elastic filament supply rolls 124 (module 10). The two elastic filaments 46' are placed under tension by conventional means in the mechanism 120, and adhesive (adhesive 44 illustrated in FIG. 3) is sprayed as each elastic filament 46' is wrapped by a sleeve portion 42 of a side margin web 34'.

Each completed side margin web 34' then is drawn through the ultrasonic bonding apparatus 110 (module 7) to be bonded to opposite sides of the nonwoven topsheet center portion web 32' as previously explained.

The ultrasonic bonding apparatus 110 also provides the inwardly located end bonds (54 in FIGS. 2 and 4) on the topsheet assembly web 30' so as to secure the standing gather ends inwardly.

As the completed topsheet assembly web 30' leaves the ultrasonic bonding apparatus 110, lines of adhesive are sprayed onto the web 30' by conventional spray adhesive appliers 134 and 138 (module 7). The adhesive applier 134 applies spaced-apart, parallel, continuous lines of adhesive 25 (FIG. 3) to the interior side of the topsheet assembly web 30' for subsequently securing the topsheet assembly web 30' to both the absorbent panel top tissue layer 27' and portions of the inner surface of the backsheet web 26' which extend laterally beyond the longitudinal edges of the absorbent panel assemblies.

The adhesive applier 138 intermittently applies short lengths of closely spaced, parallel lines of adhesive to those portions of the topsheet assembly 30' which will overlie, and be in registration with, the foam waist gather elastic elements 56 (FIG. 5). Owing to the thickness of each foam waist gather elastic element and to the degree of tension at which it is applied to the backsheet web 26', a relatively large amount of adhesive is desired in the corresponding, overlying regions of the topsheet assembly web 30'.

The completed topsheet assembly web 30' is then drawn over the laminator drum 78 in registration with the absorbent panels and underlying backsheet web 26'. Thus, all of the webs and separate component pieces carried thereon are assembled in the proper relationship at the laminator drum 78.

A conventional end seal apparatus 140 (module 7) is provided to operate in cooperation with the laminator drum 78. Owing to the degree of tension in the foam waist gather elastic element 56 and owing to the thickness of the element 56, additional compression of the element 56 is desired to ensure proper adhesive securement between the overlying topsheet assembly web 30' and the underlying backsheet web 26'. This additional compression is provided by the end seal apparatus 140.

The registered and assembled webs and other components leaving the laminator drum 78 constitute a substantially complete assembly. However, if tape tabs, such as tabs 20, are desired on the garment, then such tape tabs 20 are subsequently applied downstream of the laminator drum 78. In particular, a conventional tape tab applier 144 (module 12) applies individual pairs of tape tabs 20 in a well-known manner from a continuous tape tab web 20' which is furnished from a conventional supply roll (not illustrated). The pairs of tape tabs 20 are applied to the outer surface of the backsheet web 26'.

The web assembly next passes from the tape tab applier 144 to a conventional water knife mechanism 150 (module 13) for cutting the contoured leg cutouts 18 (FIGS. 1 and 2) along the opposite side margins of the assembled webs.

The webs are pulled along the knife mechanism 150 by a conventional draw conveyor 154 (modules 14 and 15). From the draw conveyor 154, the web assembly is fed through a conventional "C-folder" apparatus 160. The C-folder apparatus 160 folds longitudinal side margins of the webs over into a generally C-shaped configuration.

The C-folded web assembly is then carried by a conventional entry draw belt apparatus 164 (module 17) into a conventional final knife mechanism 170. The final knife mechanism 170 effects a transverse cut across the C-folded web assembly at predetermined intervals corresponding to the desired length of the completed garment or absorbent article.

A conventional exit draw belt apparatus 174, which is preferably driven in a well-known manner from the entry draw belt apparatus 164, conveys the now-severed, completed garment article from the final knife mechanism 170 to a conventional cross folder mechanism 180. The cross folder mechanism 180 folds the leading half of the garment rearwardly on top of the trailing half of the garment so that the garment is then discharged, with the folded end leading, into a conventional stacker 184. If desired, the stacker 184 may be driven from drive means provided with the main fabrication machine and controlled from the machine control system.

According to one aspect of the present invention, a novel system can be provided for operating the fabrication mechanisms for fabricating disposable absorbent articles in a machine of the type generally illustrated in FIG. 6A and 6B. The system is especially suitable for fabricating articles along at least one processing path from components which include webs of material wherein the webs are assembled by (1) a plurality of first, continuous operating means for each continuously operating on at least one moving web (e.g., a web conveyor) and (2) a plurality of second operating means for each effecting a unity operation intermittently relative to at least one associated moving web once per each absorbent article (e.g., a web severing knife).

More specifically, the system of the present invention can provide a more precise, and more easily adjustable, control of the unity operations which must be timed to occur at a precise location on, or relative to, a moving web. Such unity operations are usually controlled relative to the speed of one of the webs or other components and involve operations such as applying a tape tab, applying a foam waist gather elastic element, or transversely severing the moving webs.

In contrast, the continuous operating means are effective upon the continuously moving web components and include mechanisms such as conveyors for moving the various continuous webs along the processing line, rotating rollers or drums (such as a debulker or a laminator drum) which continuously roll against the webs, and unwind mechanisms for unwinding webs of material from supply rolls as the webs are processed.

Typically, the continuously operating means operate on moving webs at controlled speeds which can be varied depending upon the desired linear speed of the webs through the processing line. If the speeds of the webs and related continuous operating means are increased while the rates of intermittent actuation of the unity operators remain the same, then the length of each of the produced articles will be increased. Conversely, if the speeds of the webs and related continuous operating means are reduced while the actuation intervals of the unity operators remain the same, then the length of each produced article will be reduced. Of course, if the speeds of the webs and related continuous operators are increased while the actuation rates of the unity operations are correspondingly increased, then the produced article length will remain the same but the article production rate will be increased. Conversely, if the linear speeds of the webs and related continuous operating means are reduced while the rates of actuation of the unity operations is correspondingly reduced, then the produced article length will remain the same but the article production rate will decrease.

In general, it is desirable to operate a manufacturing line at relatively high speeds so as to produce completed articles at a relatively high production rate. However, as the speeds are increased, the problems associated with proper component processing, such as registration, cutting, bonding, etc., become more difficult. The system of the present invention provides improved operation and control of these processes as will next be explained.

Figure 7:
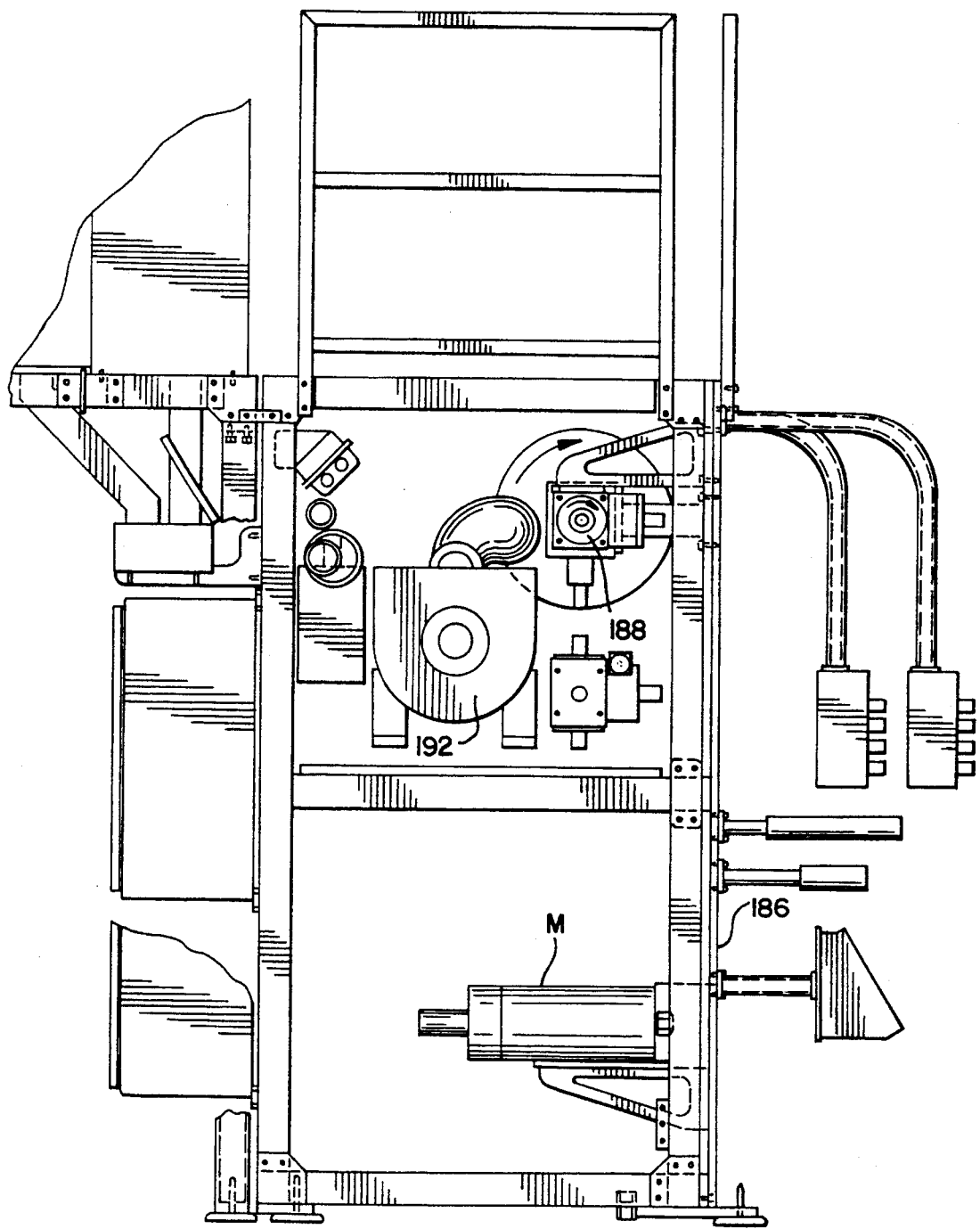
FIG. 7 is a greatly enlarged, fragmentary, simplified, partially diagrammatic view of an end of a diaper machine similar to that illustrated in FIGS. 6A and 6B.

FIG. 7 is a simplified, partially diagrammatic view of an end of a diaper machine similar to that illustrated in FIGS. 6A and 6B. According to the one aspect of the present invention, a plurality of first, continuously operating means or mechanisms are provided for each continuously engaging or otherwise operating on at least one moving web. These continuous operating means (not illustrated in FIG. 7) would be mounted to project from a vertical front wall 186 of the machine. With reference to the mechanisms shown in the machine illustrated in FIGS. 6A and 6B, such continuous operating means could include, inter alia, the bottom tissue layer web conveyor 60, the unwinding mechanism for the tissue layer supply rolls 64, the debulker 68, the unwinder mechanism for the nonwoven topsheet center portion web supply rolls 102, the pad draw conveyor 70, the pad spacing conveyor 74, the laminator drum 78, the unwinder mechanism for the nonwoven topsheet side margin web supply rolls 116, a web drive mechanism for moving the topsheet assembly web 30' past the ultrasonic bonding apparatus 110, the unwinding mechanism for the backsheet web supply rolls 80, the draw conveyor 154, and the entry draw belt mechanism 164.

The continuous operating means or mechanisms are each preferably driven by an adjustable speed DC electric motor, such as a motor M illustrated in FIG. 7. Typically, such motors M would be mounted within the machine frame and would be operatively engaged, through the front wall 186, with an associated operating mechanism, such as a conveyor, drum, unwinder mechanism, or the like (not shown in FIG. 7).

In addition, many or all of the intermittently operating mechanisms for effecting the unity operations (e.g., tape tab applier and knife mechanism) are preferably driven from a common, rotating, main drive shaft 188 (FIG. 7). The drive shaft 188 is rotated by a separate, continuous operating means, such as an adjustable speed DC electric motor 192 (FIG. 7). Such a motor can be operably engaged with the shaft 188 through a suitable power transfer device, such as a conventional endless drive belt (not shown in FIG. 7).

The main drive shaft 188 is operatively engaged with a plurality of suitable driven gear mechanisms for transferring power to the unity operation mechanisms (such unity operation mechanisms are not visible in FIG. 7). With reference to the mechanisms shown in the machine illustrated in FIGS. 6A and 6B, such intermittently operating mechanisms for effecting the unity operations can include, inter alia, the foam waist gather elastic element placement apparatus 98, the target tape placement apparatus 82, the pad severing knife mechanism 72, the end seal mechanism 140, the leg contour cutout water knife mechanism 150, the tape tab applier 144, the intermittent ultrasonic bonding mechanism for forming the standing gather inner bond 54 (FIG. 2) which is effected in the ultrasonic bonding apparatus 110, the final, web-separating knife mechanism 170, and the cross-folding mechanism 180.

Some or all of these unity operations are preferably driven from the main drive shaft 188 through directional phasing mechanical power transfer devices which are each associated with at least one of the unity operations. Any suitable special or conventional direction phasing mechanical power transfer device may be employed. One such conventional device is a speed correction gearbox manufactured by Tandler Company in the Federal Republic of Germany and sold in the United States of America by Die Qua corporation having an office at 2000 Bloomingdale Road, Glendale Heights, Ill. 60137, U.S.A. The detailed design and operation per se of such a speed correction gearbox or other direction phasing mechanical power transfer device form no part of the present invention.

In general, such a phasing mechanical power transfer device typically includes a driving bevel gear, a driven bevel gear, and a controllable intermediate bevel gear engaged between the driving gear and driven gear. The controllable intermediate gear is independently rotatable, via a separate control motor (operating in response to an externally supplied signal from a control device as explained hereinafter), to temporarily rotate the intermediate gear in one direction or the other at a speed different than the normal driven speed so as to temporarily increase or decrease the output speed of the driven gear and thereby temporarily increase or decrease the operating speed of the associated unity operating mechanism that is driven from the power transfer device. This will temporarily advance or retard the actuation of the unity operation mechanism with respect to the associated web, or other article component, that is being acted upon by the unity operation mechanism. This system can thus be used to control the actuation of a unity operation mechanism relative to a precise location on a web or other component of the article which is moving at variable speeds.

For example, consider the unity operation of the tape tab applier 144 (FIG. 6B). The tape tabs 20 (FIGS. 2 and 5) must be secured to a predetermined location along the length of the moving backsheet material web 26' relative to the absorbent panel assemblies. If the absorbent panel assemblies slip along the processing line, then the actuation of the tape tab applier can be retarded or advanced a corresponding amount by appropriately operating the intermediate gear control motor in the associated direction phasing mechanical power transfer device. Preferably, these control operations are automatically initiated through automatic electronic control devices. One such suitable device is the high speed registration device sold under the model number designation 1500 Series in the United States of America by the Hurletron Corporation having a mailing address at P.O. Box 4004, Danville, Ill. 61834-4004, U.S.A. The detailed design and operation per se of such a registration control device form no part of the present invention. Preferably, as explained in detail hereinafter, the control is initiated in response to the sensing of the actual spacing between identical portions or features of a web or other component (e.g., the leading edges of the spaced-apart moving, absorbent panel assemblies).

Figure 10:
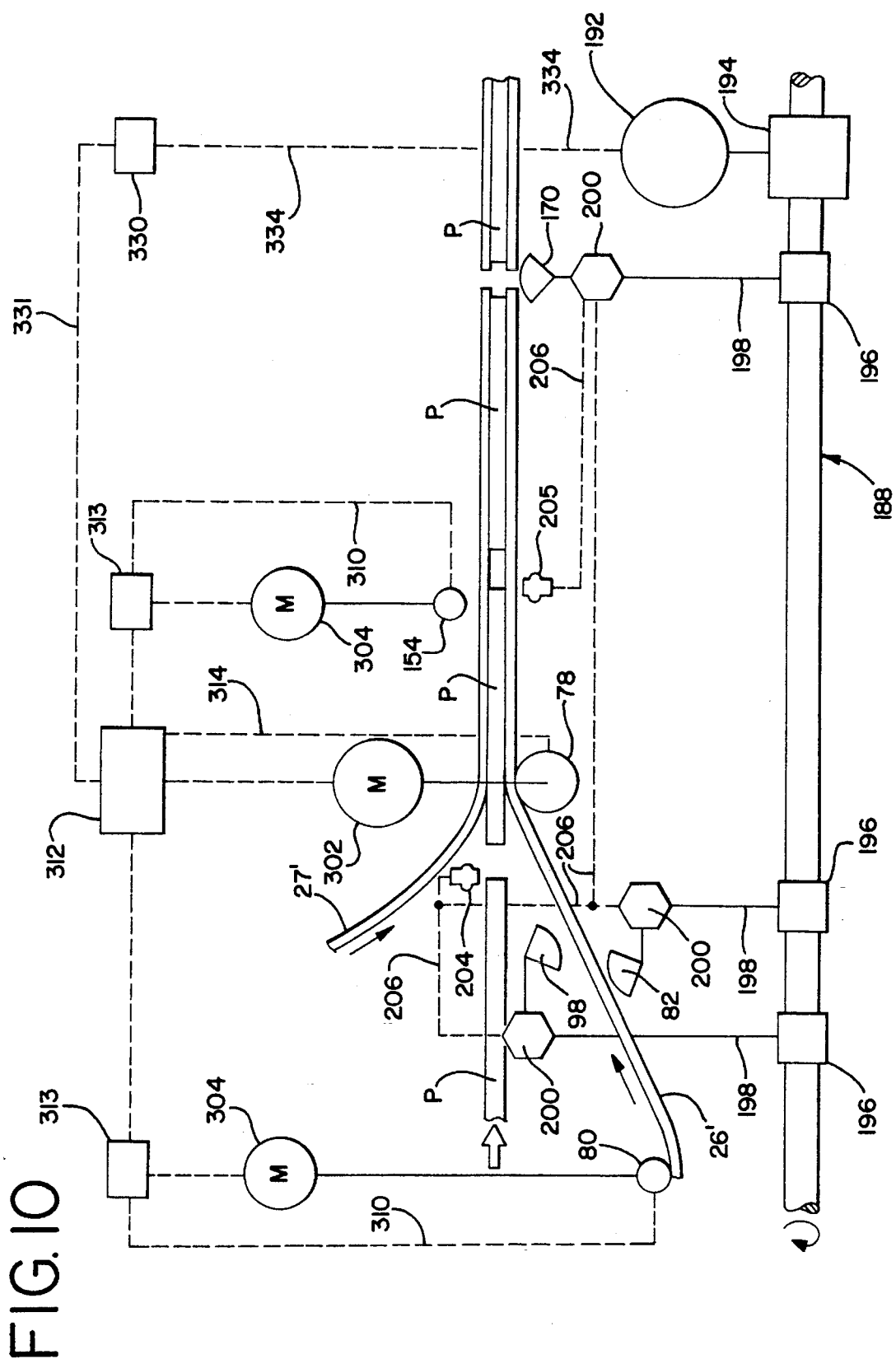
FIG. 10 is a schematic diagram of a portion of a system for operating a disposable absorbent article fabrication machine in accordance with the principles of the present invention.

FIG. 10 is a schematic diagram illustrating the principles of the operating and control system of the present invention. As an exemplification of the principles of the invention, selected continuous operating means and selected intermittent unity operating means are shown.

In particular, FIG. 10 shows a portion of the main drive shaft 188 as discussed above with reference to FIG. 7. The drive shaft 188 is rotated in the direction of the arrow 190 by the adjustable speed DC electric motor 192 operatively engaged with the shaft 188 through a suitable power transfer device 194 (FIG. 10).

The drive shaft 188 is shown driving the following devices which have been previously described: (1) the target tape applier mechanism 82 for applying target tape 22 (FIGS. 1 and 5) to the backsheet web 26'; (2) the mechanism 98 which applies the foam waist gather elastic member 56 to the backsheet 26'; and the final knife mechanism 170.

Power is mechanically transferred from the drive shaft 188 to each of the mechanisms 82, 98, and 170 via suitable power transfer devices 196 and secondary drive shafts 198. The power is indirectly transferred to each of the unity operation mechanisms 82, 98, and 170 through an associated direction phasing mechanical power transfer device 200, such as the above-described speed correction gearbox device manufactured by the Tandler Company. Many or all of the remaining unity operation mechanisms could be similarly driven from the main drive shaft 188. A separate transfer device may be employed with each unity operation mechanism. In some cases, two unity operation mechanisms may be driven from one such device.

Associated with each unity operation mechanism and power transfer device 200 is a suitable sensor means 204 for sensing the presence of a feature of one of the continuously moving webs or other components being processed. A single, common sensor 204 may be employed for all of the unity operation mechanisms. In the illustrated example in FIG. 10, the sensor 204 is located upstream of the laminator drum 78 to sense the absorbent pad assemblies.

Alternatively, one or more additional sensors, at other locations, may be employed for selected unity operation mechanisms. One such additional sensor 205 is shown for being selectively used, instead of the common sensor 204, with the final knife mechanism 170.

Each sensor 204 may include a suitable, conventional photoelectric sensor, optical scanner device, video imaging device, or the like. The detailed design and operation per se of such sensors form no part of the present invention.

Each sensor 204, 205 operates as part of a control system for adjusting the output of the associated phasing transfer device 200 as indicated by the dashed lines 206 representing a part of the control system. To this end, each sensor is preferably employed as part of an automatic control device, such as the above-described registration control device sold by the Hurletron Corporation.

The basic operation of the control system associated with the phasing power transfer device 200 and sensor 204 will next be described with reference to the target tape applying mechanism 82. As the pad assemblies P are conveyed along the processing line past the sensor 204, the shaft 188 is continuously rotating, and the target tape applier mechanism 82 is cycling through its actuation sequence at a speed proportional to the speed of rotation of the drive shaft 188. Normally, the mechanism 82 would cycle through actuation sequence of applying the target tape to the backsheet web 26' as a function of a predetermined amount of rotation of the main drive shaft 188.

The main drive shaft 188 is rotated by the motor 192 at a speed that is set, or preferably continuously controlled, to be proportional to the operating speed of the means for moving the webs along the processing path. However, if the components, such as the absorbent panel assemblies P, slip relative to the conveying system, then the target tapes applied to the web 26' will be incorrectly located relative to the slipped pad assemblies P.

This problem is corrected by employing the sensor 204 to sense the presence of a selected feature or portion of a feature of one of the components in one of the process paths. In the example illustrated in FIG. 10, the sensor 204 is adapted to sense the presence the leading edge of each passing absorbent panel assembly P. The system is initially operated to establish a desired reference spacing of the panel assemblies P. This is effected by sensing the leading edge of each panel assembly P as it passes the sensor 204. When the leading edge of a panel assembly P passes the sensor 204, the sensor 204 generates a signal which begins a timing interval. When the trailing edge of the panel assembly P passes the sensor 204, the sensor signal is terminated, but the interval continues to be timed in the control system. When the leading edge of the next, successive panel assembly P passes the sensor 204, a second signal is generated by the sensor 204, and this second signal terminates the timing interval. The length of the timing interval thus defines a reference interval that corresponds to the spacing between the successive panel assemblies P. The reference interval is recorded and stored in the control system.

During the initial reference operation of the fabrication line, the target tape applier 82 is adjusted to apply the tape at the proper location on the backsheet web 26' relative to the properly spaced absorbent panel assemblies P.

During subsequent production operations, if the panel assemblies P should slip so that the spacing between one or more of the successive pairs of panel assemblies P changes from the reference spacing, then the sensor 204 will generate its signals for the actual spacing intervals at a greater or lesser frequency corresponding to a shorter or longer spacing, respectively. The two successively generated signals define an actual measured time interval corresponding to the actual spacing. This actual measured time interval is then processed by the control system.

In particular, the control system, operating through well-known conventional means, such as the above-described automatic registration control device sold by the Hurletron Corporation, compares the measured time interval to the reference time interval and generates a positive or negative control signal proportional to the positive or negative difference between the reference time interval and the new, measured time interval. This control signal is employed to operate the associated phasing mechanical power transfer device 200 to temporarily retard or advance, as the case may be, the actuation of the target tape applier 82 so that the target tapes are applied in a manner that corresponds to the new spacing of the absorbent panel assemblies.

The foam waist gather elastic element applying mechanism 98 and the final knife mechanism 170 may be similarly controlled from the sensor 204. Further, many or all of the remaining unity operation mechanisms (which are not illustrated in FIG. 10) may be controlled from the sensor 204 in a manner similar to the above-described control of the target tape applier 82.

Alternatively, one or more of the unity operation mechanisms may be controlled from other sensors. In FIG. 10, an alternate control of the final knife mechanism 170 is illustrated as employing the alternate sensor 205 which is located downstream of the draw conveyor 154.

The final knife mechanism 170 is intermittently operated to sever the topsheet assembly web 27' and the backsheet web 26' at the appropriate locations between the ends of adjacent panel assemblies P. The alternate sensor 205 has a suitable design so that it can sense the leading edge of each absorbent panel assembly P through the adjacent covering webs, such as through the backsheet web 26'. The location of the sensor 205 further downstream than the sensor 204 results in the sensor 205 being closer to the final knife mechanism 170. This has the advantage of accommodating additional slippage, as of the panel assemblies P, that may occur downstream of the laminator drum 78, between the drum 78 and the point where the sensor 205 is located.

If the alternate sensor 205 is employed with respect to one or more unity operation mechanisms, such as with respect to the final knife mechanism 170, then a preliminary operation of the system would typically be undertaken to establish a predetermined, proper reference spacing of the leading edges of the panel assemblies P at the location of the sensor 205. The sensor 205 and control system would record the time interval corresponding to the reference spacing of the moving panel assemblies P.

The recorded and stored reference time interval, corresponding to the reference spacing of the panel assemblies P, would be used as the basis for comparison by the control system with subsequently measured actual time intervals during routine operation. The measured time intervals during routine operation may vary as a result of slippage of the panel assemblies P. The final knife mechanism 170 would be controlled via the associated phasing mechanical power transfer device 200 in response to a control signal proportional to the difference between the reference interval and the actual interval in the same manner as explained above with respect to the control of the target tape applier 82.

In FIG. 10 also schematically illustrates examples of continuous operating means or mechanisms for each continuously operating on at least one moving web. In particular, with reference to the machine components shown in FIGS. 6A and 6B, the operating control systems schematically illustrated in FIG. 10 can be employed with, inter alia, the unwind mechanism of the backsheet web supply rolls 80 and the operating mechanism for the draw conveyor 154.

Further, the overall line processing speed can be established and controlled by the continuously operating laminator drum 78. The laminator drum 78 is preferably operated by an adjustable speed DC electric motor 302, and the other continuous operating mechanisms 80 and 154 are also each preferably operated by individual, adjustable speed DC electric motors 304. One of the motors, such as the motor 302, is selected to establish a preselected speed of the associated continuously operating means which, in this case, is the laminator drum 78.

The operating speeds of the remaining continuous operating mechanisms 80 and 154 are maintained to equal the preselected speed of the laminator drum 78. In particular, this is effected by controlling the remaining motors 304 so as to adjust the speeds of the associated operating mechanisms 80 and 154.

In a preferred form of operation, the speed of the laminator drum is set by a control system 312. Further, the speed of each of the continuous operating mechanisms 80 and 154 is measured as indicated by the control signals represented in FIG. 10 by the dashed lines 310. The laminator drum set speed signal in the control system 312 is compared with each of the remaining continuous operating mechanism speed signals 310 by suitable conventional electronic feedback means 313. The speeds of the motors 304 are then adjusted as necessary so that the operating speeds of the mechanisms 80 and 154 are substantially equal to the preselected, set operating speed of the laminator drum 78 as maintained by the control system 312.

In a further preferred form of operation, the speed of the selected laminator drum 78 is also measured as indicated by the signal represented by the dashed line 314. The laminator drum 78 is then maintained precisely at the preselected speed by the associated motor 302 controlled through a suitable electronic feedback system as part of the control system 312.

The main drive shaft motor 192 is operated at a speed that corresponds to, or is proportional to, the speed of a selected continuous operating means, such as the laminator drum 78.

In a preferred form of operation, a conventional electronic feedback system is provided for directly controlling the motor 192 in response to the measured speed signal 314 of the laminator drum 78. This is illustrated in FIG. 10 by the use of a controller 330 for receiving a control signal 331 from the laminator drum speed control system 312 and providing an output control signal 334 to the drive shaft motor 192.

Although the operation and control aspects of the invention has been described or depicted for use in fabricating a specific type of absorbent garment, it will be understood that the invention can be used to fabricate other types of absorbent garments. It will be apparent that such variations, as well as other variations and modifications as come within the scope of the appended claims, can be considered part of the present invention without departing from the true spirit and scope of the novel concepts or principles of this invention.

It will be appreciated that the above-described novel operating and control system permits a single, common, main drive shaft to be employed for efficiently actuating all, or a selected number, of the unity operations (e.g., target tape applier, web severing knife, etc.). Further, the system permits the unity operations to be timed and controlled to occur at a precise location on, or relative to, a moving component of the article even when the component slips on the conveying mechanisms or when mechanical tolerances in the operating mechanisms alter the timing or stroke length of the operations.

The novel operation and control system of the present invention efficiently transfers power to the unity operators and accommodates relatively easy setting, adjustment, or continuous automatic control of the operating speeds and actuator timing. This is especially useful during start-up and when intentional, large speed changes are made.

Figure 8:
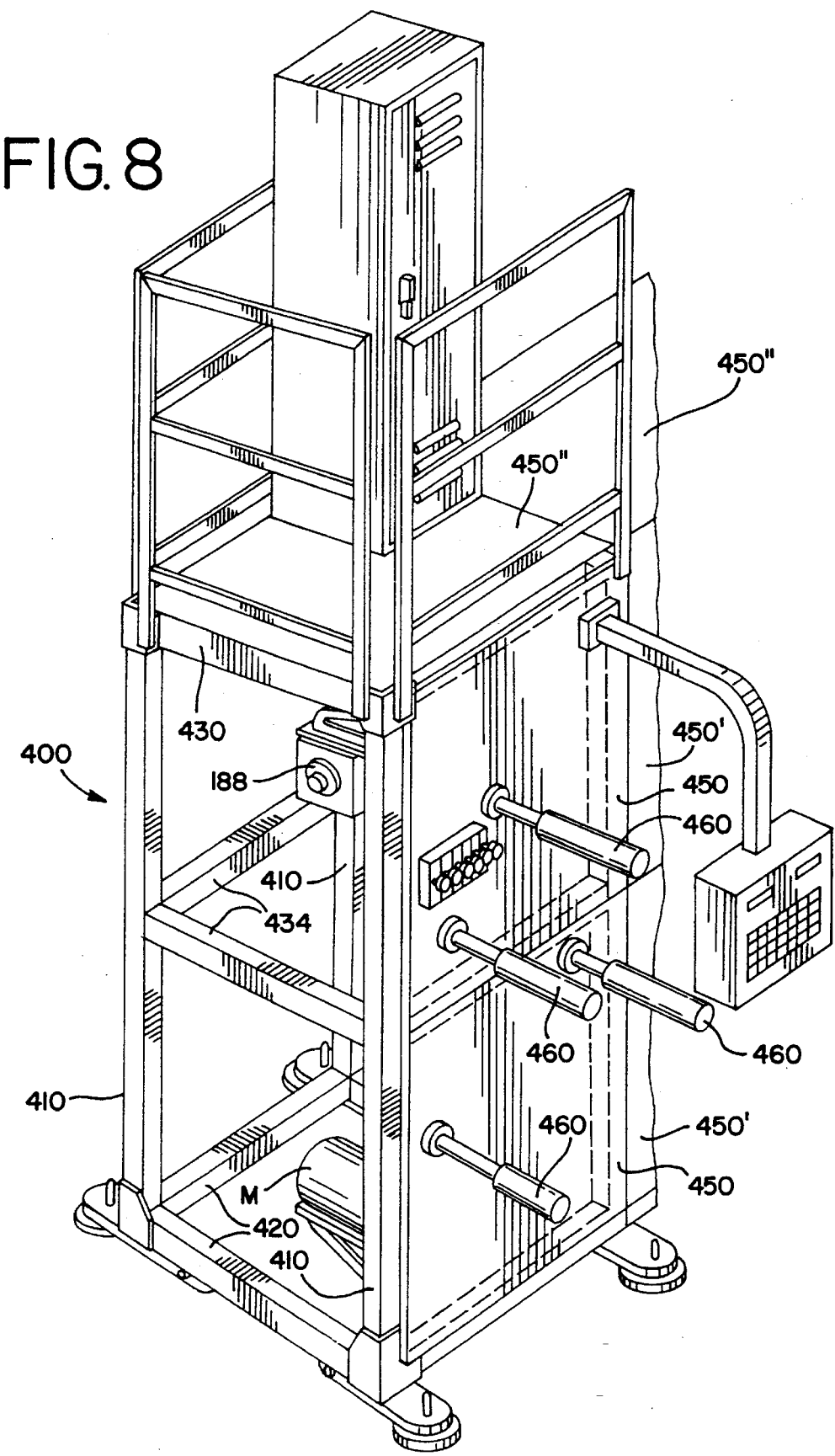
FIG. 8 is a fragmentary, perspective view of the end of a machine similar to the types of machines illustrated in FIGS. 6A, 6B, and 7.
Figure 9:
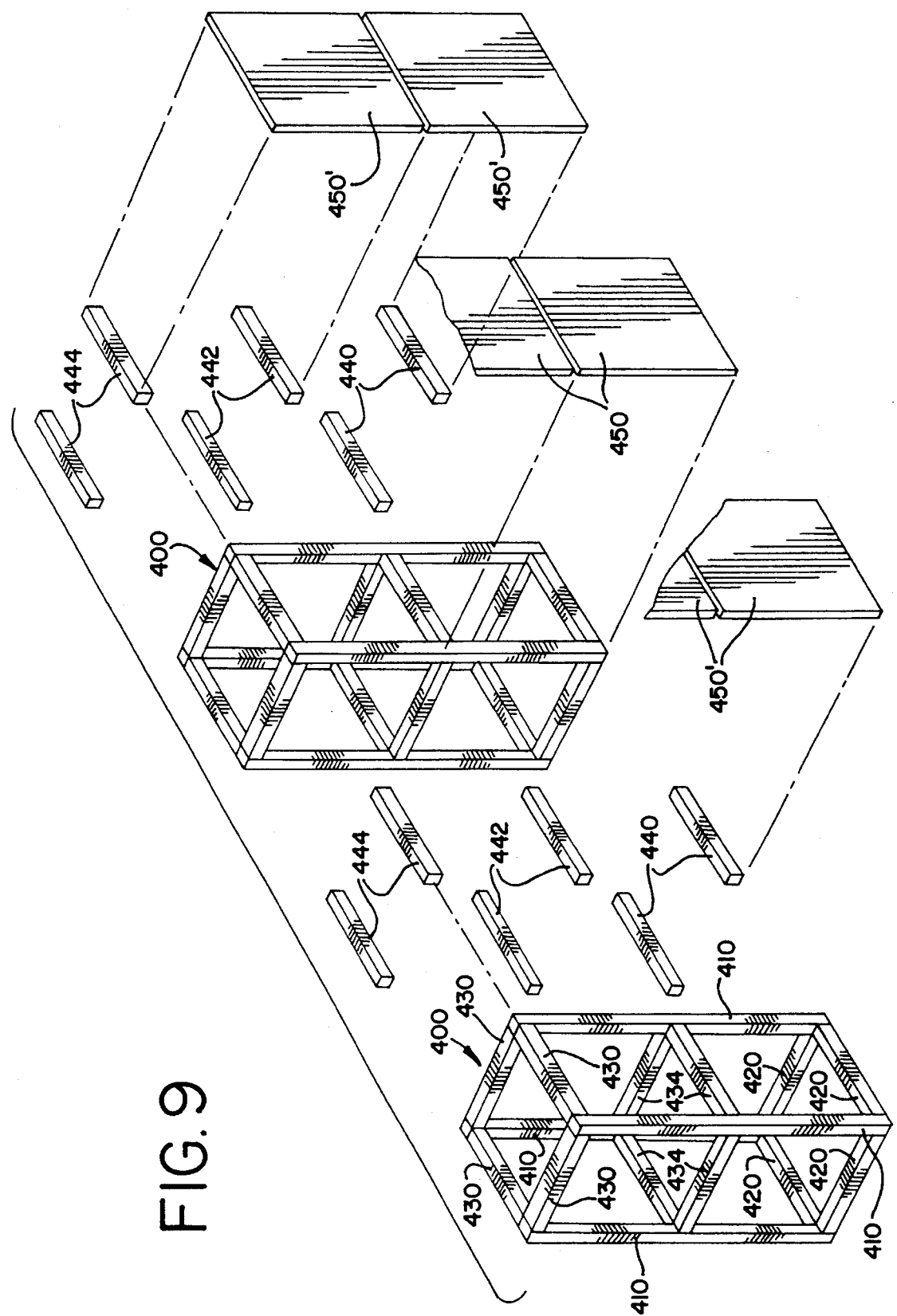
FIG. 9 is a reduced scale, simplified, diagrammatic, fragmentary, exploded, perspective view of modular support components for the type of machines illustrated in FIGS. 6A, 6B, and 8.

The above-described operation and control system can be employed with absorbent article manufacturing mechanisms in a unique support structure or supporting system for such mechanisms, or for other components and operating means, which are typically employed in the fabrication of disposable, absorbent articles. An embodiment of an unique support system, which is another aspect of the present invention, is illustrated in FIGS. 8 and 9. FIG. 8 illustrates an end portion of a fabrication machine similar to the machines described above with reference to FIGS. 6A, 6B, 7, and 10. FIG. 9 illustrates, in a greatly simplified manner, one way in which the structural members of the support system can be arranged.

The support system includes a plurality of substantially identical frame modules 400, two of which are illustrated in FIG. 9. One such module 400 at the end of an absorbent article fabrication machine is illustrated in FIG. 8 with a fabrication mechanism operating means and related apparatus shown installed thereon.

As best illustrated in FIG. 9, each module 400 has a substantially open interior and has substantially open faces. In the illustrated preferred form, each module 400 has a generally rectangular parallelpiped configuration, and the height of each module 400 is about twice the module width. In the illustrated embodiment, each module 400 has a width which is substantially equal to the module depth.

Each module 400 includes four generally vertically disposed, upright corner members 410. Preferably, the bottom ends of the upright members 410 are joined by generally horizontally disposed base members 420. Similarly, the upper ends of the upright member 410 are preferably joined by generally horizontally disposed top member 430.

If the module 400 has a rectangular parallelpiped configuration as illustrated, then additional, generally horizontally disposed, brace members 434 are preferably provided at the vertical mid point of the structure to join the central portions of the upright corner members 410. The resulting frame configuration of the module 400 has the appearance of two, stacked, hollow cubes with open faces.

As shown in FIG. 9, the preferred support system includes elongate base connecting members 440, elongate middle connecting members 442, and elongate upper connecting members 444. These connecting members extend between, and are attached to, each pair of adjacent modules 400. The members 440, 442, and 444 function, in the preferred embodiment, to space the adjacent modules apart by a distance equal to the module width, as well as to connect the modules together.

The lower connecting members 440 are positioned substantially coplaner with the bottoms of the adjacent modules 400, and the upper connecting members 444 are positioned substantially coplaner with the top faces of the modules 400. The middle connecting members 442 are substantially horizontally disposed at the mid point elevation of the modules 400 and are thus coplanar with the module mid point frame members 434.

The frame members 410, 420, 430 434, 440, 442, and 444 may have any suitable structural configuration and need not be identical. In a preferred form, the lengths of the members 420, 430, 434, 440, 442, and 440 are substantially equal for ease of manufacturing, storage, transportation, and erection. Preferably, the number of differently shaped structural members is kept to a minimum so as to simplify manufacturing, reduce inventory requirements, and facilitate installation.

Each structural member may be a special or conventional structural steel shape, and the particular configuration forms no part of the present invention. Further, conventional connections, such as bolted connections, may be employed for connecting the structural members together. Any suitable special or conventional connecting means may be employed, and the detailed nature of such connecting means forms no part of the present invention.

The modules 400 are joined together in a linear array to define a front face or wall along which the absorbent article fabrication mechanisms can be arranged. The modules 400 may be directly connected together side-by-side. However, in the illustrated preferred embodiment, the modules 400 are connected by the connecting members 440, 442, and 444 to provide a spacing equal to the module width.

A plurality of substantially identical plates or panels 450 may be mounted to the modules 400 along the front face of the array. The panels 450 are preferably substantially identical and interchangeable with respect to being selectively mountable on any selected ones of the modules 400.

In a preferred embodiment, the width of each panel 450 as measured along the length of the linear array of modules 400 is substantially equal to the module width as measured along the length of the linear array. Further, in the illustrated embodiment, each panel 450 has a generally square configuration, and each module 400 has two of the square panels 450 mounted in vertical registration to its front face.

Additional panels 450', generally identical to the panels 450, are provided for being mounted along the front face of the array between pairs of adjacent, spaced modules 400. Each panel 450' is mounted along its opposite vertical edges to the adjacent modules 400 so as to cover the module connecting members (such as members 440, 442, and 444).

Also, as illustrated in FIG. 8, additional panels 450", which are generally identical to the panels 450 and 450', can be horizontally disposed, and mounted to the tops of the modules 400 to provide a walkway and support for additional equipment, such as electrical control equipment.

The modules 400 are adapted to support the absorbent article fabrication mechanisms and other related components of an absorbent article fabrication line. For example, FIG. 8 illustrates a number of rollers or shafts 460 projecting outwardly from the front face of the panels 450. Other components, such as web conveyors, web supply rolls, ultrasonic bonding apparatus, tape tab appliers, etc. (not visible in FIG. 8), would typically be mounted to the modules 400 so as to project outwardly of the modules from the panels 450 (and from the panels 450' if employed). The mounting of the fabrication mechanisms along the front of the array of modules 400 facilitates rapid installation, servicing, adjustment of the mechanisms and accommodates convenient observation of the operation of such mechanisms.

The modules 400 also accommodate the placement of fabrication mechanism operators, such as electric motors, in the interior of the modules. One such motor M is illustrated in FIG. 8. The motor M may be supported on brackets connected to the frame members. Preferably, however, some or all of the motors are also mounted directly to the panels 450 (and panels 450' if 10 used). The motor M, and other operating means, are operatively engaged through the panels 450 with the associated absorbent article fabrication mechanisms (not illustrated).

The open frame structure of the modules 400 also readily accommodates the use of one or more drive shafts extending generally along the processing line. FIG. 8 illustrates how the main drive shaft 188, described above with reference to the machine illustrated in FIGS. 7 and 10, may be mounted within the modules 400. Other associated devices, such as gear drive assemblies, secondary drive shafts, direction phasing mechanical power transfer devices, and the like, may also be mounted within the modules 400, and are preferably mounted to the inwardly facing surfaces of the panels 450 (and 450' when used).

Preferably, the panels 450 (and 450' and 450", if employed) can be mounted to the modules 400 by a suitable special or conventional means, such as bolts or the like (not illustrated). The details of the particular panel mounting means form no part of the present invention. However, it is preferred that the particular means for mounting the panels have the capability for accommodating relatively rapid installation and for permitting removal of the panels.

One of the advantages of the modular support system of the present invention is that the panels can be mounted at selected locations to selected modules in order to support the fabrication mechanisms (and operators therefor) at the desired positions along the processing line. Further, if necessary, panels can be removed to provide even greater access to the interior of a modules 400. However, owing to the fact that each module 400 is typically open on the back, access for routine inspection or maintenance would not normally require removal of the front panels.

The modular system of the present invention is also adapted to accommodate expansion or contraction of the fabrication line. Modules can be removed from the array or added to the array as needed. Further, the machine electrical frame need not be intimately attached to the machine frame, and a variety of flexible design arrangements are thus possible with this modular system.

It will be readily apparent from the foregoing detailed description of the invention and from the illustrations thereof that numerous variations and modifications may be effected without departing from the true spirit and scope of the novel concepts or principles of this invention.

What is claimed is:

1. A system for in-line fabrication of disposable absorbent articles, said system comprising:

a plurality of substantially identical frame modules each having an open interior and open faces, said modules being joined in a linear array to define a front face therealong;

a plurality of substantially identical panels each mounted to one of said modules along said front face of said array, said panels each being selectively mountable on selected ones of said modules;

absorbent article fabrication mechanisms arranged for in-line fabrication of said absorbent articles and mounted to project from said panels outwardly of said modules to facilitate operator access to said mechanisms; and a plurality of operating means for operating a plurality of said mechanisms, said operating means being mounted inside said modules and operatively engaged through said panels with said mechanisms.

2. The system in accordance with claim 1 in which each said panel has an inner surface facing inwardly toward the interior of the module to which it is mounted; and said system includes mounting means for mounting at least one of said operating means to said panel inner surface.

3. The system in accordance with claim 1 in which the width of each said panel as measured along said linear array is substantially equal to the module width as measured along said linear array.

4. The system in accordance with claim 1 in which the height of each said module is substantially equal to twice the panel height.

5. The system in accordance with claim 1 in which each said panel is a generally square, flat plate.

6. The system in accordance with claim 1 in which at least some of said panels each have a generally square configuration; and some of said modules each have two of said square panels mounted in vertical registration to a front face of the module.

7. The system in accordance with claim 1 in which said system includes elongate connecting members extending between, and attached to, each pair of adjacent modules for spacing said adjacent modules apart by a distance equal to the module width as measured along said linear array.

8. The system in accordance with claim 7 further including additional ones of said panels each disposed along said front face of said array between a pair of adjacent, spaced modules and mounted thereto.

9. A system for supporting components of a machine for in-line fabrication of disposable absorbent articles, said system comprising:

a plurality of substantially identical frame modules, each said module including elongate frame members disposed generally along edges of a parallelpiped and joined together to form a generally open framework having open front and rear faces, open side faces, and open top and bottom faces;

connecting means for connecting said modules in a linear array with said front faces aligned in a generally common plane;

a plurality of substantially identical panels for each being selectively associated with a selected one of said modules and means for mounting each of said panels to said front face of an associated module;

absorbent article fabrication mechanisms arranged for in-line fabrication of said absorbent articles and cantilevered from said panels outwardly of said modules to facilitate operator access to said mechanisms; and a plurality of operating means for operating a plurality of said mechanisms, said operating means being mounted inside said modules and operatively engaged through said panels with said mechanisms.

10. The system in accordance with claim 9 in which said connecting means includes a plurality of elongate connecting members extending between, and attached to, each pair of adjacent modules.

11. The system in accordance with claim 9 in which said connecting means connects said modules together at equally spaced-apart intervals with the spacing between each pair of adjacent modules as measured along the linear array being substantially equal to the width of each module as measured along the linear array.

12. The system in accordance with claim 11 in which additional ones of said panels are each disposed along said front face of said array to each extend across one of said intervals between a pair of adjacent modules.

13. The system in accordance with claim 9 in which said system includes upper attaching means for attaching one of said panels generally horizontally to one of said modules to cover at least a portion of said open top face.

\* \* \* \* \*